US006654643B1

(12) United States Patent
Schmid (10) Patent No.: US 6,654,643 B1
(45) Date of Patent: Nov. 25, 2003

(54) INSULATION PIERCING ELECTRICAL CONTACT, ESPECIALLY FOR MEDICAL DISPOSABLE ARTICLES SUCH AS FETAL SCALP ELECTRODES

(75) Inventor: Alfons Schmid, Boeblingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/980,808

(22) PCT Filed: Oct. 8, 1999

(86) PCT No.: PCT/EP99/07546

§ 371 (c)(1),
(2), (4) Date: May 29, 2002

(87) PCT Pub. No.: WO00/64340

PCT Pub. Date: Nov. 2, 2000

(30) Foreign Application Priority Data

Apr. 22, 1999  (EP) .............................. 99107961

(51) Int. Cl.[7] .......................... A61N 1/05; A01B 5/0444
(52) U.S. Cl. ..................... 607/116; 600/376; 439/909
(58) Field of Search ................................ 600/373, 376, 600/382, 383, 386; 439/909

(56) References Cited

U.S. PATENT DOCUMENTS

| | | | | | |
|---|---|---|---|---|---|
| 3,842,394 | A | * | 10/1974 | Bolduc | 439/261 |
| 4,148,540 | A | * | 4/1979 | Hayes | 439/425 |
| 4,204,741 | A | * | 5/1980 | Hall | 439/278 |
| 4,314,737 | A | * | 2/1982 | Bogese et al. | 439/425 |
| 4,703,989 | A | * | 11/1987 | Price et al. | 439/283 |
| 4,715,825 | A | * | 12/1987 | Mouissie et al. | 439/391 |
| 5,061,202 | A | * | 10/1991 | Nemcovsky | 439/404 |
| 5,445,535 | A | * | 8/1995 | Phillips et al. | 439/394 |

FOREIGN PATENT DOCUMENTS

| | | | | | |
|---|---|---|---|---|---|
| DE | 29706108 | | * | 9/1997 | ......... A61B/5/0416 |
| EP | 0131705 | | * | 1/1985 | ............ H01R/4/24 |
| EP | 0571639 | | * | 12/1993 | ............ H01R/9/07 |
| WO | 98/29031 | | * | 7/1998 | ......... A61B/5/0408 |

* cited by examiner

Primary Examiner—Jeffrey R. Jastrzab
(74) Attorney, Agent, or Firm—John Vodopia (57) ABSTRACT

The insulation piercing electrical contact in accordance with the invention consists of a first contact element (20) for establishing an electrical contact with a second contact element (30), a contacting member (50) piercing an electrical conductor (60, 63) when the two contact elements (20, 30) are joined. The first contact element is provided with a molding (20) that encloses the electrical conductor (60, 63) at the contact side and electrically insulates it.

24 Claims, 7 Drawing Sheets

INSULATION PIERCING ELECTRICAL CONTACT, ESPECIALLY FOR MEDICAL DISPOSABLE ARTICLES SUCH AS FETAL SCALP ELECTRODES

BACKGROUND OF THE INVENTION

The present invention relates to contact elements for establishing an electrical contact in that, when the contact elements are joined, a contact element cuts into or pierces an electrical conductor.

Plug-type connections generally are disengageable or non-disengageable electrical connections of one or more contacts, electrical contact being established by inserting complementary contact elements, such as a plug and a socket, one into the other.

In the case of disengageable contacting a connection is regularly established in that one contact element bears resiliently against the other element or is clamped onto the other element. In this respect there are many alternatives such as, for example sockets and resilient pins, resilient sockets and pins, leaf springs on pads, shear clamps, wire clamps, pin clamps, screw-type clamps for wires or pins and so on. Plug-type connections of this kind are customarily provided for numerous insertion and withdrawal cycles.

As opposed to the disengageable electrical connections, in the case of non-disengageable electrical connections an electrical contact is to be established that is regularly only a one-time, non-disengageable electrical connection. Among the non-disengageable electrical connections there are notably the piercing clamping connections where a one-time contact is established through an insulated cable by means of a piercing element. Contacting normally takes place in the direction perpendicular to the sheath of the electrical conductors.

Finally, in addition to the disengageable or non-disengageable electrical connections in the strict sense of the word there are also hybrid forms that are designed for more or less numerous insertion and withdrawal cycles, for example, piercing clamping connections that are intended for a given number of insertion and withdrawal cycles. Piercing clamping connections of this kind are described inter alia in EP-A-131705 or WO 98/29031.

Nowadays a typical example of a disengageable electrical connection is encountered in the medical field for the purpose of birth monitoring, that is, for the so-called fetal galea or scalp electrodes for monitoring the fetal cardiac activity. The fetal scalp electrode is used to record the ECG of the unborn child by means of two electrodes. At the side of the scalp electrodes there are provided two open (bared) tinned wires for contacting two resilient jaws as counter contacts at the apparatus side. Applicant discloses fetal scalp electrodes of this kind inter alia in U.S. Pat. No. 5,423,314 or U.S. Pat. No. 3,750,650.

The fetal scalp electrode customarily is a disposable product; therefore, like other medical disposable articles it should be as inexpensive as possible. The simple bare contact wires satisfy this cost requirement.

International regulations, such as imposed by the FDA (Food and Drug Administration) or MDD (Medical Device Directive), stipulate that the open, electrically conductive wires of the fetal scalp electrodes must be replaced by an insulated plug-type connector so as to protect the patients against incorrect contacting.

A further requirement that is imposed in particular on fetal scalp electrodes is that the plug element should be as small as possible, because must be easy to pull this element through an inner tube of an introduction instrument in the known embodiments.

A plug-type connection of this kind for fetal scalp electrodes that notably satisfies said safety regulations is known from EP-A-484107. According to that plug-type connection system the two wires are connected to insulated sockets (in conformity with the known jack plug connection), said sockets subsequently being placed on pins. This arrangement, however, has the drawback that, because of the necessary limitation of the dimensions of the plug element, its manufacture is intricate and hence expensive.

SUMMARY OF THE INVENTION

Therefore, it is an object of the present invention to provide a method of electrical contacting that on the one hand enables the use of insulated plug-type elements, for example, in order to satisfy said safety regulations, and on the other hand enables plug elements to be proportioned so as to be as small as possible. The method of contacting in accordance with the invention should also enable the manufacture of as inexpensive as possible plug-type contacts that are notably suitable for medical disposable articles such as, for example fetal scalp electrodes. This object is achieved as disclosed in the characterizing part of the independent claims. Advantageous embodiments are disclosed in the dependent claims.

The invention is based on the idea to design the plug element of a clamping piercing connection that consists of a plug and a socket to be such that the plug element is enclosed by a molding, prior to the establishment of an electrical contact, in such a manner that electrical conductors of the plug (at least those that are to be contacted) are completely electrically insulated at the contact side. Electrical contact is then established by the piercing of or cutting into the corresponding electrical conductors of the plug by contact elements. The molding may be designed so as to be connected to and integral with the plug conductors or as separate parts, and is preferably essentially complementary to a corresponding recess in the socket in which the plug is to be inserted for the purpose of contacting. Depending on the relevant design, the plug can be introduced into the socket in the pulling direction of the plug conductors, in the direction perpendicular thereto or at an arbitrary angle; pull-out forces for separating the connection and/or for pulling out the cables can be defined and determined by suitable design.

According to the known clamping piercing connections (see notably the cited EP-A-131705 or WO 98/29031), usually only the cables that are insulated by way of the cable insulation are pierced by appropriate knives and the end of the electrical conductors at the contact side, which is usually only cut off, can thus give rise to undesirable electrical contacts. In contrast therewith, however, the molding in accordance with the invention also provides electrical insulation for the end of the electrical conductors at the contact side, thus enabling undesirable electrical contacts to be avoided.

Because of the essentially complementary design of the molding and the corresponding socket recess, moreover, the clamping piercing operation can be specified and concretized in defined insertion positions. Furthermore, suitable codes and/or locking mechanisms can be used in conformity with the relevant application.

The solution in accordance with the invention is particularly suitable to enable the safety contacting necessary for fetal scalp electrodes. However, the solution in accordance with the invention is not restricted to medical applications in general or to fetal scalp electrodes in particular, but is suitable for all disengageable plug-type connections where only a small number of insertion and withdrawal cycles is required at the plug side. This concerns notably disposable articles or other applications where it is necessary to establish a disengageable contact which, however, as a rule is closed or opened only once or a few times.

When the solution in accordance with the invention is used, notably in the case of fetal scalp electrodes, it is ensured that the safety regulations can be met at low costs. Moreover, the electrical connection operation is significantly simplified for the user. Because the user normally wears protective gloves and such gloves are moist because of the vaginal introduction of the fetal scalp electrode, it is not easy to control the customarily used spring jaws and the insertion of the bared wires. This situation is significantly improved by means of a plug-type connection in accordance with the invention, because the user can reliably control the plug with one hand only.

Depending on the relevant field of application, the solution in accordance with the invention enables low-cost manufacture of the plug contacts that are to be used for small numbers of insertion and withdrawal cycles. The invention notably enables very inexpensive manufacture of only a part of the plug-type connection, that is, preferably the insulated plug element. The second part of the plug-type connection can then be manufactured at costs that correspond to those of the solutions used at present (for example, the costs of tinning the bared wires correspond to the costs of molding a plug in accordance with the invention around the cable). This means that the advantage of the basic idea of the solution in accordance with the invention may reside notably in the costs of such plug-type connections where, for example, the costs of the plug should be low and the plug is required for a small number of insertion and withdrawal cycles only. The invention is thus particularly suitable for disposable articles of the kind frequently used for reasons of hygiene in the medical field.

A preferred embodiment of a plug-type connection in accordance with the invention is provided on the one side (at the cable side) with a plug element that is arranged on a cable (preferably not bared) and is preferably molded on the cable while using a synthetic material, and on the other side (the side to be contacted) with a socket element for receiving the plug element. A suitable bond can be realized between the plug element and the cable insulation notably when the same synthetic material is used for the plug element and for the cable insulation. The plug element at the side of the cable is formed in such a manner that it can be preferably inserted into the opening of the socket element so as to be locked against rotation. During the insertion operation a piercing contact member that projects into an open space of the socket element pierces the cable conductor through the insulation and hence establishes an electrical connection between a contact element of the socket element and the cable conductor. Similarly, in the case of a plurality of cable conductors a plurality of piercing contact members may be provided, each of said members establishing a respective electrical connection between a corresponding contact element of the socket element and the relevant cable conductor.

The socket element in a preferred embodiment is formed as a removable or exchangeable element so as to enable a fast exchange of the socket, for example, in the case of deterioration of the piercing intensity or for the purpose of cleaning or sterilization of the socket element. In conformity with the relevant application, the socket element may also be constructed as a disposable product.

The socket element in another embodiment can be connected in a plug-type fashion to a connection element, for example, to a measuring apparatus or a leg plate (in the case of the fetal scalp electrode) so as to ensure a fast and simple exchange. A possibly specified pull-out force can then be realized by way of an appropriate design and/or proportioning of this plug-type connection; the socket element then becomes disengaged from the connection element under the influence of pulling. This may be necessary or desirable notably in the case of medical applications such as the fetal scalp electrode.

The plug is preferably designed in such a manner that it still has an electrically insulating effect even after execution of a number of piercing clamping operations, be it in some cases to a limited extent only. This effect can be achieved, for example, by way of a suitable choice of the materials and/or dimensions of the cable insulation and/or the molding, so that, for example, the cable insulation and/or the molding return to their initial position (prior to the establishment of the piercing clamping connection) to a given degree after the disengaging of the clamping piercing connection. Furthermore, the risk of undesirable electrical contacts after the disengaging of the piercing clamping connection can be mitigated by providing suitable air gaps.

BRIEF DESCRIPTION OF THE DRAWINGS

The invention will be described in detail hereinafter with reference to the drawings in which corresponding references relate to functionally identical or similar characteristics.

DETAILED DESCRIPTION OF THE DRAWINGS

Figure 1:
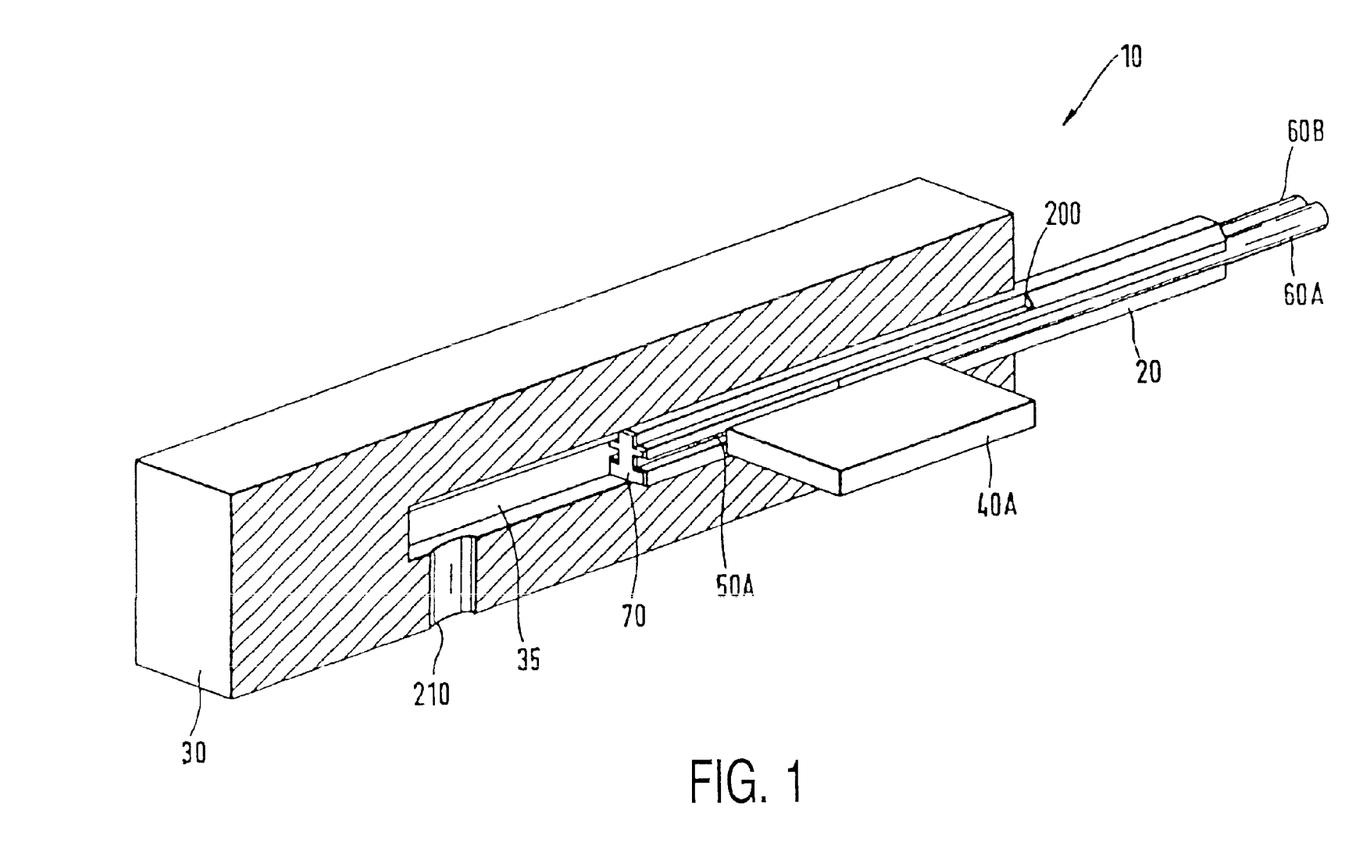
FIG. 1 shows a preferred embodiment of an electrical plug-type connection 10 in accordance with the invention.

FIG. 1 shows a preferred embodiment of an electrical plug-type connection 10 in accordance with the invention. A plug element 20 (also referred to merely as plug hereinafter) is inserted partly into a socket element 30 (also referred to hereinafter merely as socket) that is shown in a cut-away view. The shapes of the plug 20 and the socket 30 are adapted to one another; the terms plug and socket in this context have to be understood in such a manner that the plug element can be introduced (or plugged) into a socket channel 35 of the socket element. A contact element 40A that is connected to the socket 30 supports, at its side that faces the plug element 20, a piercing (contact) element 50A that is only partly visible in FIG. 1. The piercing element 50A serves to establish, in the state of contact, an electrical contact between the contact 40A (preferably to be fed out) of the socket 30 and at least one corresponding electrical conductor of the plug 20.

Figure 2:
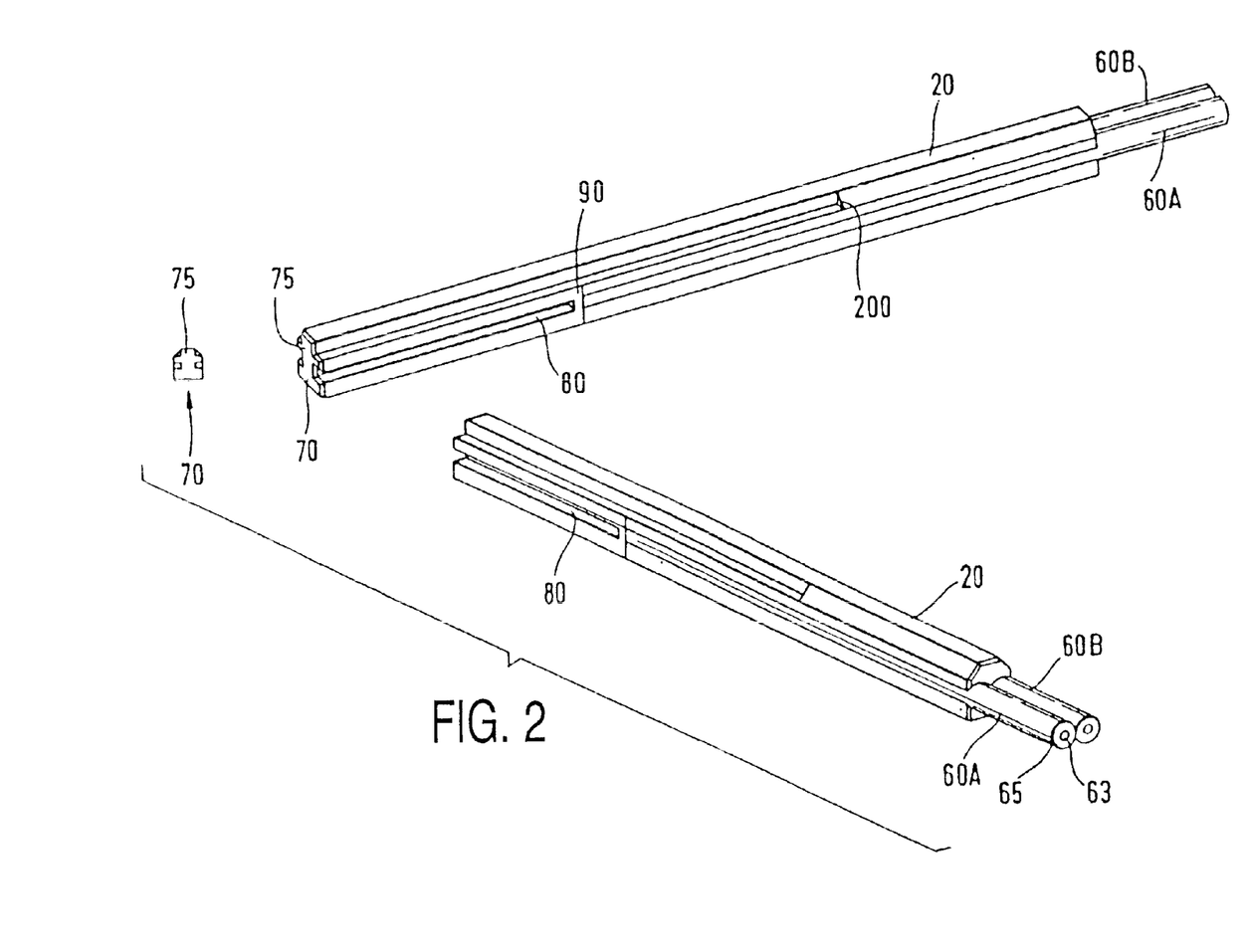
FIG. 2 shows more detailed views of the plug element 20 that is shown in FIG. 1, FIGS. 3A and 3B are more detailed views of the socket 30 that is shown in FIG. 1, FIGS. 4A and 4B show alternative embodiments of piercing elements 50.

In the embodiment that is shown in FIG. 1 the plug 20 comprises two cables (or wires) 60A and 60B, each of which contains sheathed and hence insulated electrical conductors (see 63 in FIG. 2). The piercing element 50A of the contact 40A serves to establish an electrical contact with the conductor 60A and a further contact 40B with a corresponding piercing element 50B (not visible in the representation chosen for FIG. 1) is intended to contact the conductor 60B.

The plug element 20 is preferably formed by molding around the insulated cables 60, for example, while using a synthetic material; this enables economical manufacture of the plug element 20. Instead of the two insulated wires 60A and 60B that are shown in FIG. 1, one or more wires 60 can be used in conformity with the relevant application.

FIG. 2 shows more detailed views of the plug element 20 that is shown in FIG. 1. The external shape of the plug element 20 is essentially complementary to the internal shape of the socket 30 so as to ensure insertion of the plug 20 and the socket 30 one into the other.

The plug element 20 of the preferred embodiment that is shown in the FIGS. 1 and 2 preferably has an external shape that is suitable to lock the position of the plug element 20 relative to the socket element 30 and to preclude undesirable rotation. In the case of a plurality of cables 60, for example, it can thus be ensured that the individual cables 60 are contacted with the correct polarity or that the corresponding contacts 40 are associated with the respective individual cables 60. In the example that is shown in the FIGS. 1 and 2 the end face 70 of the plug element 20 that faces the socket 30 is shaped in the form of two letters F that are turned upside down and mirrored relative to one another or, in other words, as a letter T that stands on its head and is provided with a central stroke that extends parallel to the horizontal stroke of its head. A resultant head section or strip 75 that is not situated axially symmetrically (and above the upper horizontal stroke in FIG. 2) relative to a corresponding central horizontal H (in the insertion direction) thus ensures that the plug 20 is inserted into the socket 30 with the correct orientation.

Appropriate shaping of the plug element 20 (notably in conformity with the end face 70) also enables codes to be realized for different types of plug so that, for example, undesirable connection to an inappropriate socket 30 is prevented.

For the case where the plug element 20 need not be locked against rotation, the plug element 20, and notably the end face 70, can also be axially or point symmetrically configured, so that the contacting between the plug element and the socket 30 can take place at a plurality of angles of rotation, for example, of each time 180°. In that case, for example, an H-shape (for example, resting on its side as shown in FIG. 2) or the like would be suitable.

The suitably realized design of the plug element 20 (preferably by enrobing or molding around the cables 60) includes at the plug side the insulated cables 60, fixes the position thereof and provides support. At the side of the plug element 20 at which the piercing contact element 50 penetrates the relevant wire 60 there is preferably provided a recess or cut-out 80 that serves to prevent the knife or knives 50 from being unnecessarily burdened prior to the actual contacting.

In order to ensure adequate insulation of the cable ends of the cables 60 in the plug direction, these cable ends preferably are not fed as far as the end face 70, but only as far as a position that is situated at a selectable distance therefrom. In order to enhance the insulation further, in a preferred embodiment a thin layer 90 of preferably a synthetic material is provided between the end of the relevant cable 60 and said cut-out 80.

As is shown in the lower part of FIG. 2, the cables 60 are preferably composed of a respective (electrical) conductor 63 and an insulation 65 that envelops the conductor 63. The conductor 63 may be a single conductor or may consist of a plurality of individual conductor fibers or litzwires. However, the invention is not limited to the contacting of cables of the kind that is shown in FIG. 2; arbitrary other cables can also be used. Notably the plug element 30 need not adjoin the insulation 65, but may rest also directly against the conductor 63 so that use can also be made, for example, of cables wherefrom the insulation 65 has been removed at the plug side.

Figure 3A:
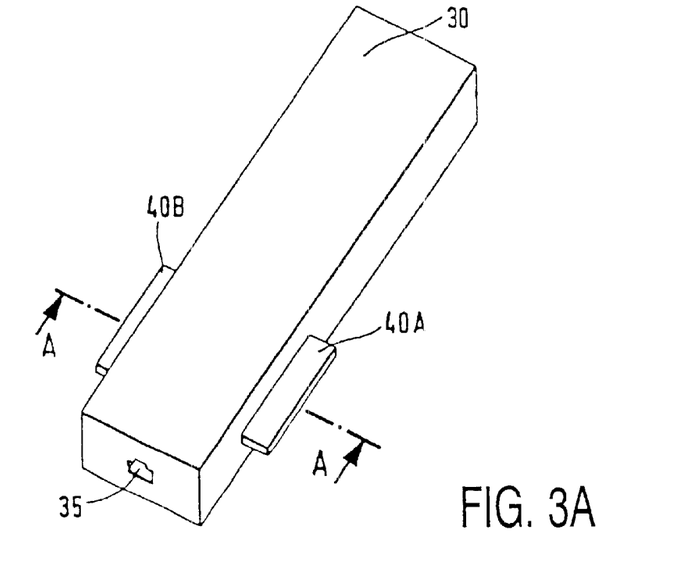
Figure 3B:
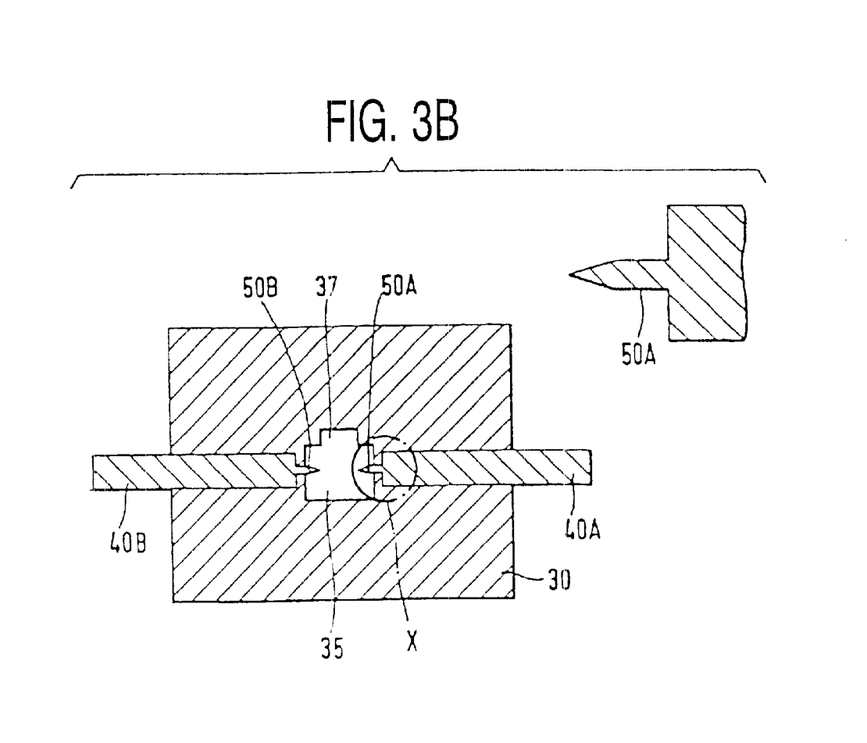

The FIGS. 3A and 3B are more detailed representations of the socket 30 that is shown in FIG. 1; FIG. 3A is a perspective view of the socket 30 and FIG. 3B is a cross-sectional view, that is, a view taken at the area A—A and in the viewing direction indicated by the arrow A. The contacts 40A and 40B are provided at opposite sides of the socket channel 35 and the piercing elements 50A and 50B both project into the socket channel 35.

The shape of the socket channel 35 corresponds essentially to the shape of the plug 20 so as to ensure easy insertion of one into the other. The shape of the socket channel 35 should also be aimed, if desired, at achieving possible locking against rotation and/or at encoding of the plug 20 and, therefore, is provided with appropriate elements for locking against rotation and/or for decoding. In the embodiment that is shown in the FIGS. 3A and 3B the socket channel 35 is provided, in correspondence with the shape of the plug 20 that is shown in FIG. 2, with a cut-out 37 that is complementary to the strip 75.

In the FIGS. 3A and 3B the end of the contacts 40 that is remote from the piercing elements 50 is fed out of the housing of the socket 30 for the purpose of external contacting. However, arbitrary other ways of feeding out of the same contacts 40 from the socket 30 are feasible in conformity with the relevant application. For example, the contacts 40 can be fed through in the socket 30 in the direction of the cable axis within the socket 30 and be fed out from a side of the socket 30 that opposes the side of the socket channel 35 where the plug insertion opening is situated.

Contacting is realized by inserting (see FIG. 1) the plug 20 of FIG. 2 into the socket element 30 (see FIG. 3B). The piercing (contact) elements 50 are preferably constructed as knives 50 and are arranged in such a manner that during the insertion operation they first slide into the cut-out or slit 80 (see FIG. 2) of the plug 20, after which they penetrate to a given depth (for reasons of safety so as to ensure protection against touching) into the insulated cable 60 so as to establish (electrical) contact.

Figure 4A:
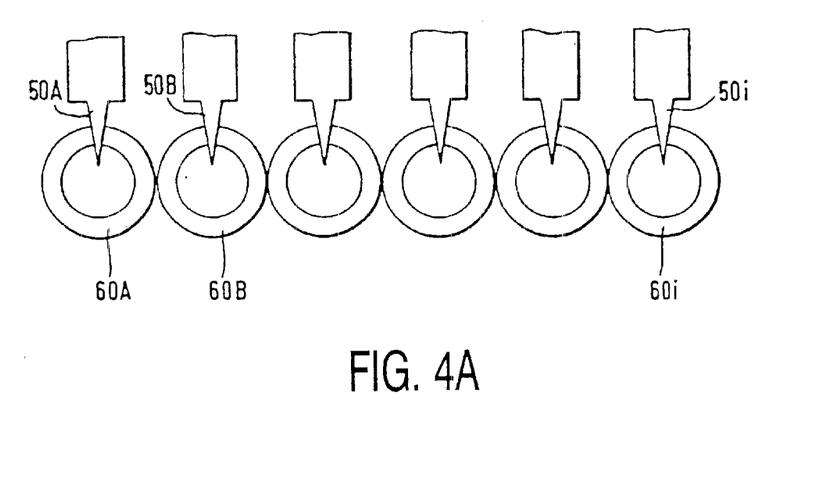
Figure 4B:
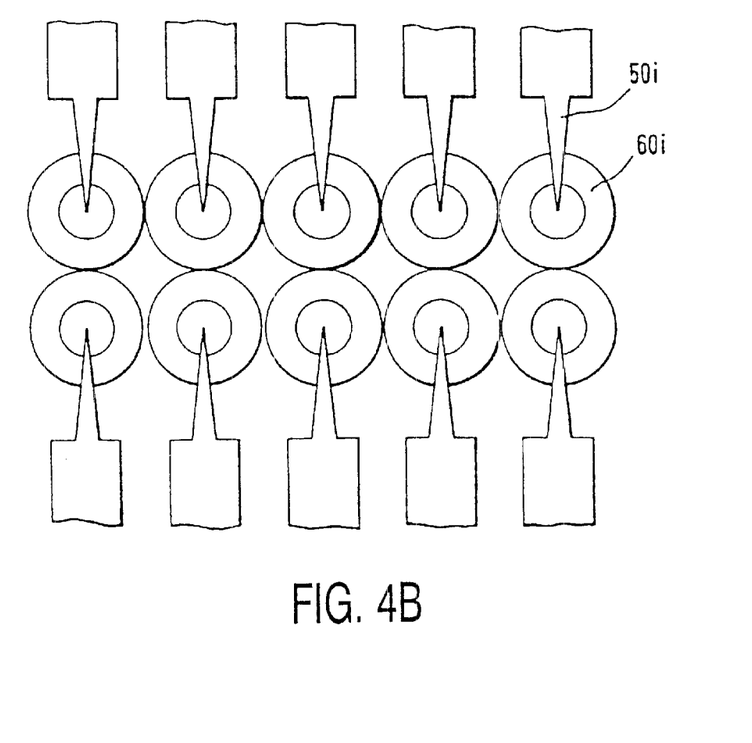

The FIGS. 4A and 4B show alternative embodiments of piercing elements 50 for the contacting of cables with a plurality of individual cables 60$i$ (where i=A, B, . . . ). In FIG. 4A the cables are arranged parallel to one another in a row. In conformity therewith the socket 30 is provided with a plurality of piercing contact elements 50$i$ that are concatenated in a row. In FIG. 4B, however, the plug 20 comprises two mutually parallel rows of cables 60$i$ and, in conformity therewith, the socket 30 comprises a respective row of piercing contact elements 50$i$ above and below the cable rows 60$i$.

In a preferred embodiment the same material, preferably a synthetic material, as used for the plug element 20 is used for the insulation of the cables 60$i$; when a synthetic material is used, the plug element 20 is preferably molded around the cables 60$i$ while using this synthetic material. A very good bond can be ensured between the relevant materials when the materials for the sheathing/insulation of the cables 60*i* and of the plug element 20 are suitably chosen and preferably the same materials are used for these elements.

The piercing contact elements or knives 50*i* in a preferred embodiment are made of a material that is very hard and non-corrosive and ensures a suitable contact. Furthermore, the contact knives 50*i* are shaped in such a manner that they remain sharp as long as possible, thus ensuring that an adequate number of insertion and withdrawal cycles can take place.

The presence of the recesses 80 and the associated exact, sufficiently long guiding of the plug element 20 in the socket channel 35 of the socket element 30 ensure that no transverse forces are exerted on the piercing elements 50*i* of the contacts 40*i*, so that fracturing of the piercing elements 50*i* can be avoided. For the piercing elements 50*i* themselves a distinction must be made between the cutting part and the part that establishes the contact. The cutting part should be as long as possible so as to ensure that it always comprises a sharp section, whereas the part that establishes the contact should extend as slanted as possible, for example at an angle of less than 45°, relative to any litzwires present in the cables 60*i*, thus avoiding the necessity of splitting of all fibers (or litzwires) at the same time.

Figure 5:
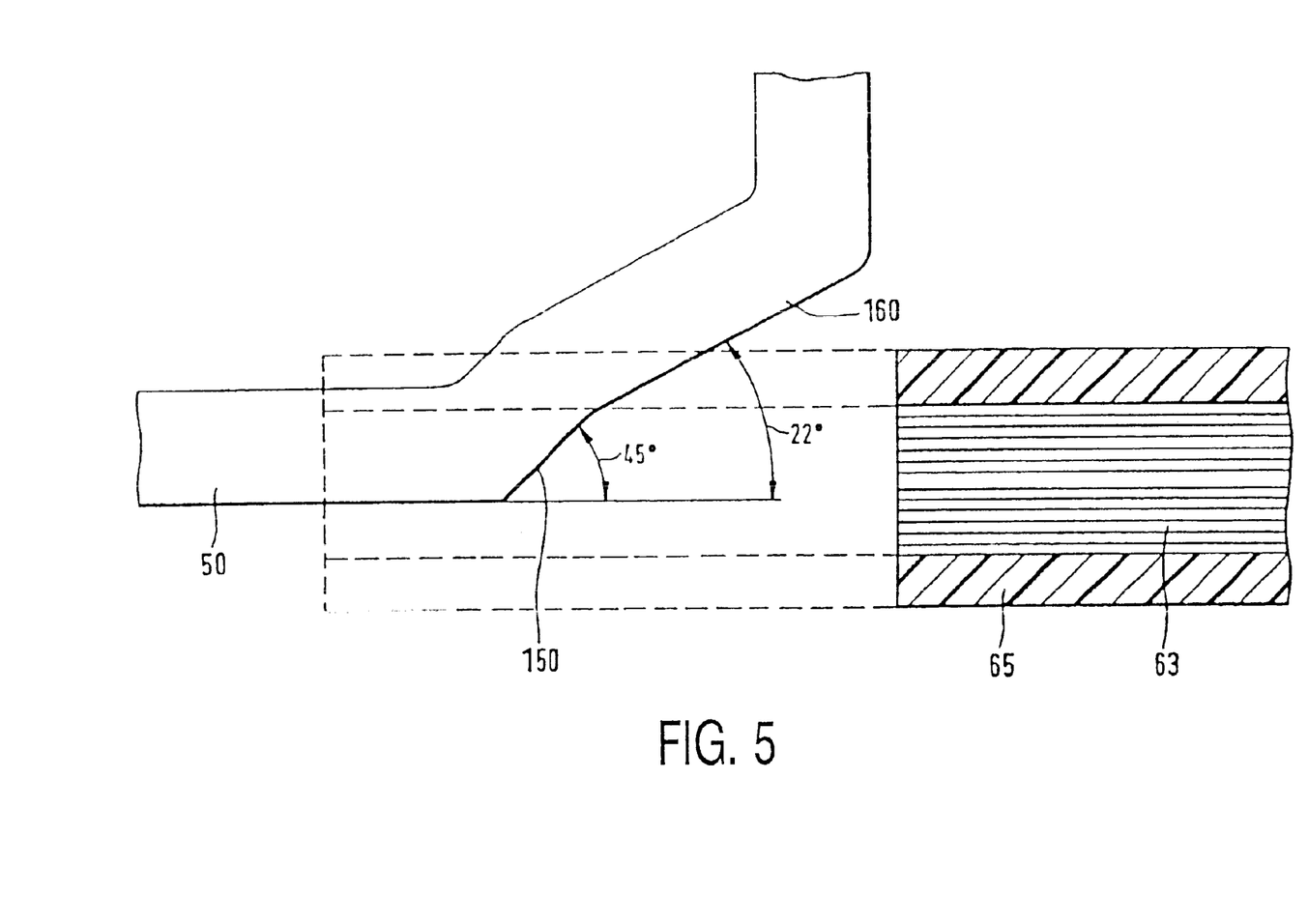
FIG. 5 shows a suitable design of a piercing element 50.

FIG. 5 shows a suitable design of a piercing element 50. The piercing element comprises a first section that extends preferably at an angle of from approximately 40 to 50° (preferably 45°) and serves to contact the conductor 63 of the cable 60. The first section 150 is adjoined by a second section 160 which extends preferably at an angle of from approximately 10 to 30° (preferably 22°) and serves to pierce the insulation 65 and a small part of the conductors 63. Experiments have demonstrated that 600 insertion and withdrawal cycles are easily possible when the piercing element is formed in this manner.

Figure 6:
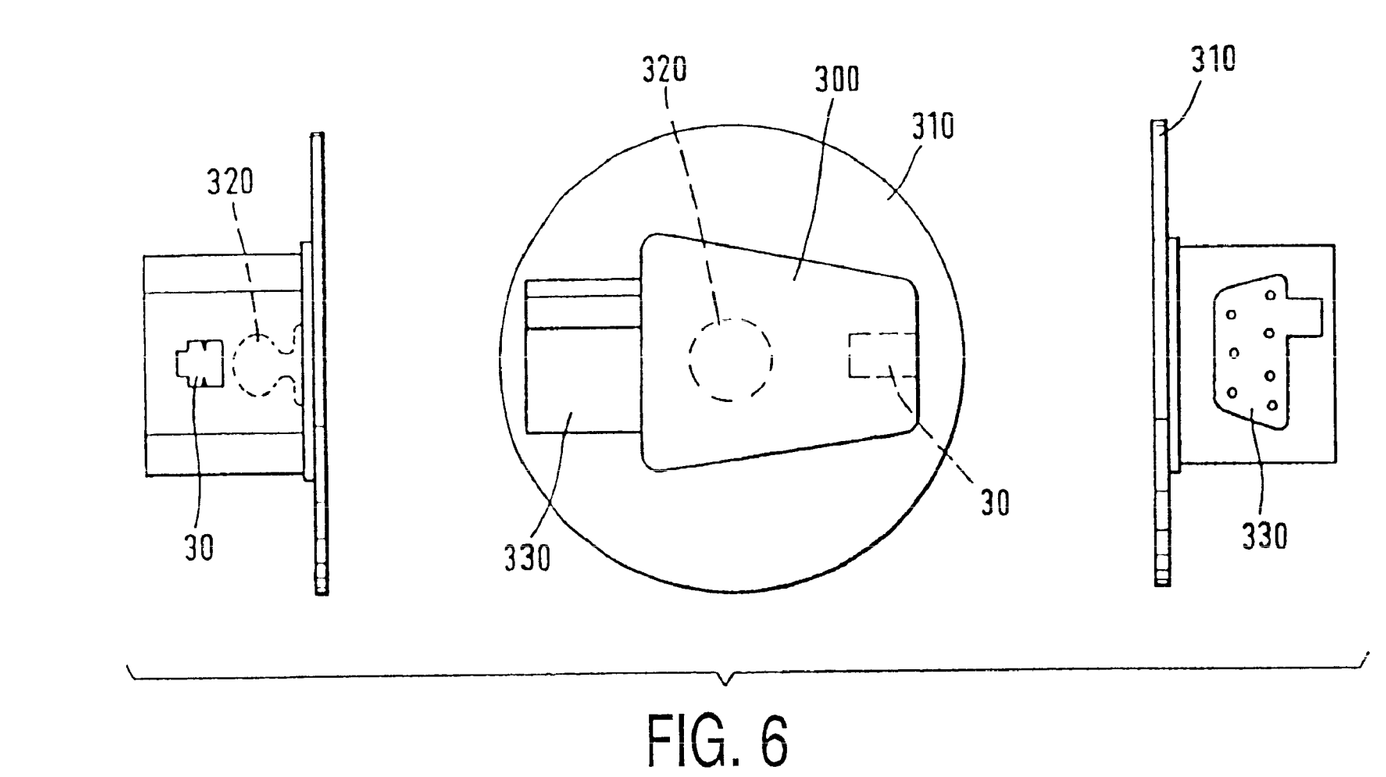
FIG. 6 shows an embodiment of the socket element 30.

FIG. 6 shows a plan view and side elevations of a preferred embodiment of the socket element that enables the plug 20 to be detached from the socket element 30 when it is pulled in the opposite direction. This solution also enables easy replacement of the socket element 30, for example in the case of a deteriorating piercing intensity or for the purpose to cleaning or sterilizing the socket element 30. A member 300 that is made of a synthetic material and supports the socket 30 in accordance with the invention on one side is snapped onto a support 310 (such as, for example a standard ECG adhesive electrode) by means of a snap fastener 320. In the case of the standard ECG adhesive electrode 310, it forms in conjunction with the member 300, for example, a passive leg plate for attachment to the leg of the patient. Preferably, on its other side the member 300 is provided with a further contact connection 330, for example a socket in conformity with U.S. Pat. No. 5,615,674.

When the element 20 and the socket 30 are joined and a pulling force is exerted, for example, on the cable 60 (not shown in FIG. 6), the member 300 of a synthetic material is rotated in the pulling direction around the snap fastener 320. Consequently, the pulling force is always applied in the pull-out direction of the plug 20, thus enabling easy opening of the plug-type connection.

The plug 20 is preferably retained in the socket 30 by the frictional forces that are produced by the piercing operation. However, in addition to or instead of this clamping connection there may also be provided a different retaining system, for example, by locking and/or fastening (for example, by way of trunnions or pins).

A preferred embodiment of a contacting system in accordance with the invention will be described in detail hereinafter, by way of example, for the contacting of a fetal scalp electrode. Reference is made in particular to the FIGS. 1 to 3 and 5, said Figures, however, not being limited to the application involving the fetal scalp electrode.

The plug element 20 (being the less expensive element) is provided with the cut-outs 80 for the piercing elements 50 at the right and the left in the representation of FIG. 2, said piercing elements being shown on the side of the socket in the FIG. 3. At the area of the cut-outs 80 the piercing elements 50 are free and do not engage the plug 20. When the plug 20 is inserted further into the socket 30 (beyond the area of the cut-outs 80), the preferably very short insulation layer 90 is cut through, the conductors 63 of the cables 60 that are provided with the insulation 65 are pierced and the contact with the copper wires of the conductor 63 is established when the plug element 20 is inserted further.

In the upper region of the plug 20 there is provided the strip 75 and in the upper region of the socket channel 35 there is provided the cut-out 37 that is complementary to said strip 75; these elements thus serve to provide locking against rotation and to improve the guiding between the socket 30 and the plug 20, it thus being ensured that the plug can be inserted into the socket 30 in one orientation only.

A stop 200 for the plug 20 as shown in the FIGS. 1 and 2 is provided so as to stop the insertion operation. The stop 200 of the plug 20 then abuts against the front face of the socket 30 that faces the plug. This stop 20 makes sense notably in the case of the fetal application, because in the case of contamination of the socket channel 35, the contamination can be pushed into the rear area of the socket channel 35 wherefrom it can be discharged via an opening 210 as shown in FIG. 1. Such discharging would not be ensured in the case of abutment against the end face of the socket channel 35.

In order to form the plug element 20, the cables 60A and 60B as shown in FIG. 1 are arranged in a suitable tool and are kept in position at the left and the right. Subsequently, an injection molding operation is performed while using a synthetic material, thus forming a connection between the member of synthetic material and the insulation 65 of the cables 60. The plug 20 thus becomes mechanically stable so that it can be readily inserted into the socket 30. A cable sleeve or protection against kinking may also be provided, but is not necessary for the application involving a fetal scalp electrode, because the plug 20 required for this purpose is preferably very small and ductile.

The socket 30 that is provided for the contacting of the plug element 20 with the fetal scalp electrode is constructed in conformity with the FIGS. 3A and 3B, but may also have a different construction. The piercing elements 50 that are rigidly connected to the contacts 40 are preferably molded so as to be fixed in the correct position in the socket 30. The piercing elements 50 themselves preferably have the shape that is shown in FIG. 5.

The socket 30 itself is preferably snapped, together with a standard fetal socket 330 in conformity with U.S. Pat. No. 5,615,674 in a member 300 of a synthetic material, onto a standard ECG adhesive electrode 310 by means of a snap fastener 320. The standard ECG adhesive electrode 320 constitutes, in conjunction with the member 300 of a synthetic material, a passive leg plate for attachment to the leg of the patient.

Figure 7A:
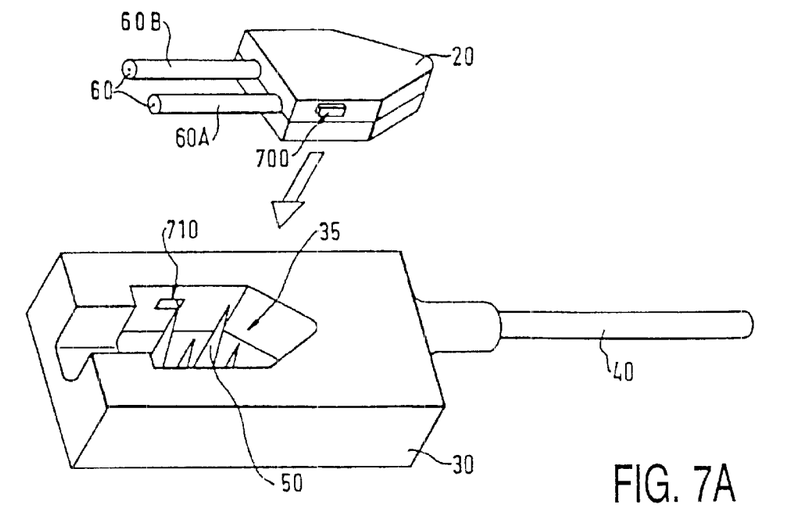
FIGS. 7A to 7C illustrate a further embodiment of the invention.
Figure 7B:
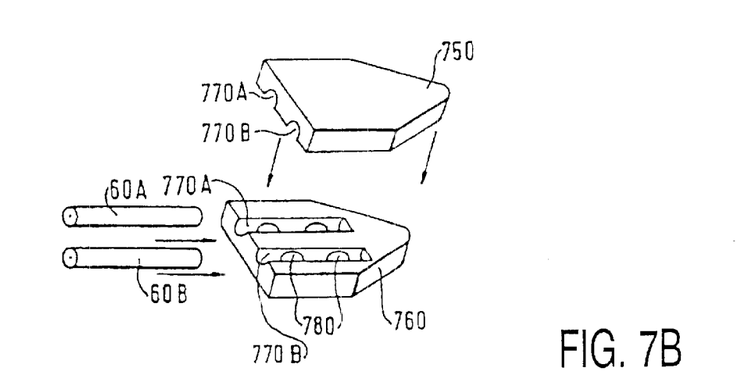
Figure 7C:
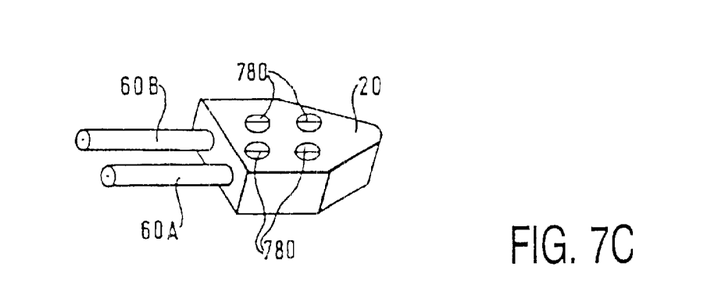

The FIGS. 7A to 7C show a further embodiment of the invention. Whereas the contacting operation in the clamping/plug-type connection that is shown in FIG. 1 takes place essentially in the direction of the cable axis, the contacting operation in the clamping/plug-type connection that is shown in FIG. 7 takes place essentially in the direction perpendicular to the cable axis.

In the 3-dimensional representation of FIG. 7A the plug element 20 is inserted into the socket channel 35 of the socket element 30 in the direction of the arrow. In the contacting state piercing elements 50 establish an electrical contact between contacts 40 of the socket 30 that are fed out via a cable and the corresponding electrical conductors 60 of the plug 20. The plug 20 and the socket 30 in the embodiment that is shown in the FIG. 7 both comprise two insulated cables.

Because of the essentially complementary design of the plug 20 and the socket channel 35, the electrical contacts of the plug 20 and the socket 30 are already rigidly related to one another, so that in the case of a plurality of cables to be contacted there are only two possible combinations, that is, in conformity with the direction of insertion that is shown in the FIGS. 1 and 7A or with the plug 20 rotated through 180° around the cable axis. In conformity with the foregoing, these possible combinations can be limited to one permissible combination by appropriate encoding or by taking other suitable steps.

In FIG. 7A such a limitation of the possible combinations is preferably realized by way of a nose or projection 700 in the plug element 20; this projection 700 co-operates, when introduced from the correct side (in FIG. 7A the plug 20 should be rotated to 180° for this purpose), with a corresponding cut-out or recess (not shown in FIG. 7A) in the socket channel 35. Instead of such encoding, or in combination therewith, the projection 700 may also be constructed so as to be resilient, with the result that it can co-operate with a corresponding recess 710 in the socket channel 35 and engages, in the case of a correct direction of insertion, in the recess 710 as from a given, selectable feed-in depth, for example, in the sense of a snap connection. If no insertion code is provided, the projection 700 may be configured so as to be so elastic that both insertion directions are permitted. In this case locking takes place in the first insertion direction (when the projection 700 and the recess 710 are appropriately brought together), thus possibly increasing the safety, whereas the second insertion direction (without bringing together the projection 700 and the recess 710) is also permitted, be it without locking.

The plug 20 and the socket 30 are joined in the direction of the arrow in FIG. 7A. In order to establish the electrical contacts, the plug 20 is then pressed against the piercing elements or knives 50 that are present in the socket channel 35. In the embodiment that is shown in FIG. 7A each time two knives 50 are provided for each cable 60, said knives being applied at different positions in the cable direction. Joining can be realized simply by pressing by hand or by means of a suitable device such as a lever mechanism or the like. Furthermore, after successful joining of the plug 20 and the socket 30, the connection can be protected against the penetration of contaminations and/or undesirable opening by way of a suitable cover or a lock. The cover/lock can also be given a disconnect/eject functionality so that separation of the plug 20 and the socket 30 is mechanically assisted.

FIG. 7B is an exploded view of a preferred embodiment of the plug 20 that is shown in FIG. 7A. The plug 20 is in this case composed of an upper section 750 and a lower section 760. For the assembly of the plug 20 the two (insulated) cables 60A and 60B (analogously, only one or more than two cables could be involved) are inserted into correspondingly designed cable ducts 770A and 770B in either the upper section 750 or the lower section 760, which section is subsequently combined with the corresponding counter part of the plug 20 (also provided with corresponding cable ducts 770A and 770B), the upper section 750 and the lower section 760 thus fixing the cables 60A and 60B. The pull-out force that is required for pulling out the cables 60 (against the direction of the arrow) can be adjusted by appropriate proportioning of the fit between the upper section 750 and the lower section 760 (notably of the diameter of the cable ducts 770A and 770B). Similarly, a non-detachable connection or a more or less readily detachable connection can be realized between the upper section 750 and the lower section 760 by appropriate shaping and design of the upper section 750 and the lower section 760, so that after assembly the plug 20 is configured as a disposable product or as a possibly re-usable product.

FIG. 7C shows a special embodiment of the lower section 760 that is shown in FIG. 7B, be it rotated through 180° and already connected to the cables 60 and to the upper section 750. The lower section 760 is provided with at least one cut-out 780 for each cable 60 at the area of the cable duct 770, so that the knives 50 can directly pierce the cable insulation and need not first cut through the plug 20. The knives 50 are thus spared. Moreover, the plug 20 can then also be constructed so as to have thicker walls and/or that it can be punched from a harder material.

As is shown in FIG. 7A, the socket 30 and the plug 20 can both be constructed in such a manner that they are situated at the cable ends of the cables 40 and 60.

What is claimed is:

1. A first contact element for establishing electrical contact with a second contact element, wherein the second contact element defines a contact channel and includes a contacting member projecting into the contact channel, the first contact element comprising:

an electrical conductor having a contacting side; and a molding enclosing at least the contacting side of the electrical conductor, said first contact element being shaped such that the contacting side of the electrical conductor is insertable into the contact channel of the second contact element to an inserted position such that the electrical conductor is pierceable by the contacting member in the second contact element when the first contact element is inserted to the inserted position, the molding having a cut-out area in which the contact element of the second contact element is receivable during a partial insertion of the first contact element such that the electrical conductor is not pierceable during the partial insertion of the first contact element, the molding further having a thin layer of material, between the end of the electrical conductor at the contact side and the cut-out area.

2. A second contact element for establishing electrical contact with a first contact element, the first contact element having an electrical conductor that is completely electrically insulated by a molding in a portion of the first contact element, the second contact element comprising:

a socket defining a contact channel shaped for receiving the first contact element along an insertion direction; and a contacting member projecting into the contacting channel for piercing the electrical conductor disposed in the first contact element when the first contact element is received in the contact channel to establish electrical contact between the contacting member and the electrical conductor, the contacting member comprising a first section extending at an angle of 40 to 50 degrees relative to the insertion direction and a second section extending at an angle of 10 to 30 degrees relative to the insertion, wherein the second section is arranged to pierce the molding and the first section is arranged to make electrical contact with the electrical conductor of the first contact element when the first contact element is received in the second contact element.

3. A second contact element for establishing electrical contact with a first contact element, the first contact element having a conductor that is completely electrically insulated by a molding in a portion of the first contact element, which is being received by the second contact element, the second contact element comprising:

a socket defining a contact channel for receiving the first contact element;

a contacting member projecting into the contacting channel for piercing the electrical conductor disposed in the first contact element when the first contact element is received in the contact channel to establish electrical contact between the contacting member and the electrical conductor; and said socket further defining a passage disposed between an exterior area surrounding the second contact element and the contact channel for the discharge of material collected in the contact channel, the passage being disposed in a face distal from an opening of the contact channel where the first contact element is received.

4. A first contact element for establishing an electrical contact with a second contact element, the second contact element including a contacting member and a contacting channel into which the contacting member projects, the first contact element comprising:

a carrier comprising an electrically insulating molding and having a central axis, the carrier being removably engageable in the contacting channel of the second contact element to an insertion position so that the first contact element is multiply engageable and disengageable with the second contact element; and a conductor terminated in the carrier and comprising a receiving section carried by the carrier, the receiving section being receivable with the carrier in the contact channel of the second contact element, and the molding being piercable by the contacting member when the carrier is engaged to the inserted position so that electrical contact is establishable between the contacting member and the conductor, the receiving section being completely electrically insulated by the molding to avoid electrical contact before being first received with the carrier in the second contact element and being substantially electrically insulated when disengaged after being received.

5. The first contact element of claim 4, wherein said carrier defines a guide slit formed so that the contacting member is guidable in the guide slit, said guide slit being arranged to be insertable in the second contact element ahead of the conductor.

6. The first contact element of claim 5, the wherein the molding includes a wall disposed between the guide slit and the conductor relative to the longitudinal direction of the carrier.

7. The first contact element of claim 4, wherein the carrier comprises a cross-section comprising a shape so as prevent rotation in the second contact element while engaged in the second contact element.

8. The first contact element of claim 7, wherein the cross-section comprises an asymmetrical shape wherein the shape is asymmetrical relative to the central axis of the carrier, the asymmetrical shape for one of preventing rotation in the second contact element while engaged in the second contact element and providing a detectable code.

9. The first contact element of claim 4, wherein the carrier comprises an abutment transverse to the central axis of the carrier so as to define a first and a second longitudinal portion of the carrier, wherein only the first longitudinal portion is receivable in the second contact element.

10. The first contact element of claim 4, wherein the carrier comprises a cross-section substantially complementary to a receiving space of the second contact element.

11. The electrical contact device of claim 4, wherein the conductor comprises an electrical insulation and the molding encloses the electrical insulation.

12. The first contact element of claim 11, the electrical insulation and the molding are integrally formed by injection molding with a synthetic material.

13. The first contact element of claim 4, wherein the conductor comprises an electrical insulation and the molding is secured to the electrical insulation by one of a clamping, crimping, and snapping connection.

14. The first contact element of claim 13, wherein the molding comprises a first and a second part surrounding the electrical insulation of the conductor.

15. The first contact element of claim 4, wherein the molding comprises a synthetic material for completely electrically insulating the conductor before being received in the with the carrier in the second element.

16. The first contact element of claim 4 further comprising a plurality of conductors, each conductor terminated in the carrier and comprising a receiving section carried by the carrier, each receiving section being receivable in the second contacting element with the carrier and pierceable by a respective contacting member disposed in the second contact element to establish electrical contact with the second electrical contact element, the respective receiving sections being completely electrically insulated by the molding to avoid electrical contact before being first received with the carrier in the second contact element and being substantially electrically insulated when disengaged after being received.

17. The first contact element of claim 4, wherein the conductor comprises an electrical insulation and the molding comprises a cut-out arranged over the electrical insulation so that the electrical insulation is pierceable by the contacting member when the carrier is engaged to the insertion position.

18. A second contact element for establishing an electrical contact with a first contact element, the first contact element carrying a conductor that is completely electrically insulated by a molding in a portion of the first contact element which is being received by the second contact element, the second contact element comprising:

a socket defining a contact channel for releasably receiving the first contact element along a longitudinal axis, the contact channel comprising a shape that prevents rotation of the first contact element with respect to the second contact element and receives the first contact element in only one direction; and a contacting member extendable in the contacting channel for piercing the molding to make electrical contact with the conductor when the first contact element is received in the contact channel, the socket being multiply engageable and disengageable with the first contact element.

19. The second contact element of 18, wherein the contacting member comprises a first section extending at an angle of 40 to 50 degrees relative to the longitudinal axis and a second section extending at an angle of 10 to 30 degrees relative to the longitudinal axis, wherein the second section is arranged to pierce the molding and the first section is arranged to make electrical contact with the electrical conductor of the first contact element when the first contact element is received in the second contact element.

20. The second contact element of 18, further defining a passage for discharging effluent collected in the contact channel, the passage providing communication between an exterior of the second contact element and the contact channel, the passage being disposed in a face of the contact channel distal from an opening of the contact channel in which the first contact element is receivable.

21. The second contact element of 18, further comprising means for disengageably coupling to a further device to make the second contact element interchangeable.

22. The second contact element of 21, where the means for disengageably coupling comprises plug-type connector.

23. The second contact element of 18, wherein said contacting member and contact channel are arranged for creating a frictional force for retaining the first contact member when the first contact member is received in the contact channel.

24. A fetal scalp electrode, comprising:

a first contact element including a carrier comprising an electrically insulating molding and a conductor terminated in the carrier and comprising a receiving section carried by the carrier; and a second contact element including a contact channel for releasably receiving the carrier including at least the receiving section of the first contact element to an inserted position and a contacting member extending into the contacting channel, the contacting member arranged for piercing the molding of the first contact element to make electrical contact with the conductor when the first contact member is received in the inserted portion, wherein the receiving section of the conductor is completely electrically insulated by the molding to avoid electrical contact before being received in the second contact element and substantially electrically insulated when disengaged after being received in the second contact member, and wherein the first and second contact elements are multiply engagable and disengageable.

* * * * *